United States Patent
Alamna et al.

(10) Patent No.: US 7,285,396 B1
(45) Date of Patent: Oct. 23, 2007

(54) Aβ-HEME PEROXIDASE

(75) Inventors: Hani Alamna, Albany, CA (US); Bruce Ames, Berkeley, CA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 46 days.

(21) Appl. No.: 11/395,925

(22) Filed: Mar. 30, 2006

(51) Int. Cl.
*C12Q 1/28* (2006.01)
(52) U.S. Cl. .......................................................... 435/28
(58) Field of Classification Search ..................... None
See application file for complete search history.

(56) References Cited

OTHER PUBLICATIONS

Atamna et al. PNAS 2006;103(9):3381-3386.*

* cited by examiner

*Primary Examiner*—Ralph Gitomer
*Assistant Examiner*—Bin Shen
(74) *Attorney, Agent, or Firm*—Richard Aron Osman

(57) ABSTRACT

Aβ-heme peroxidase activity is selectively measured and inhibited, packaged as a pharmaceutical composition with heme biosynthetic cofactors or as an industrial enzyme, and used to oxidize target substrates.

4 Claims, No Drawings

Aβ-HEME PEROXIDASE

BACKGROUND OF THE INVENTION

The field of the invention is a novel peroxidase.

Intracellular amyloid-β peptide (Aβ) and its aggregates are thought to be the neurotoxic agents in Alzheimer's disease (AD) (1-3). Important cytopathologies in AD include loss of iron homeostasis; mitochondrial complex IV dysfunction; oxidative stress (4-7); and cholinergic, dopaminergic, and serotonergic dysfunctions. These cytopathologies play a role in subsequent cognitive impairment (8). Although the molecular link between Aβ and the important cytopathologies seen in AD is not fully understood, our earlier work produced strong evidence that heme may play a key role in the molecular link between Aβ and these cytopathologies. We found that heme metabolism is altered in AD brain (9); that the complex phenotype of heme deficiency (10, 11) is associate with important cytopathologies in AD (10, 11); and that heme readily binds with Aβ, forming an Aβ-heme complex (9). We proposed a model in which excessive Aβ in AD brain binds to regulatory heme, creating a functional heme deficiency (9). Frey and coworkers (12) demonstrated the inactivation of muscarinic acetylcholine receptors by oxidative damage catalyzed by a low-molecular weight substance enriched from AD brain; heme was proposed to be involved in this inactivation. It has been previously demonstrated that heme prevented aggregation of $Aβ_{(1-40)}$ and $Aβ_{(1-42)}$ (13). We have published aspects of the present invention (Atamna H & Boyle, K (2006) Proc Natl Acad Sci USA 103, 3381-3386).

BRIEF SUMMARY OF THE INVENTION

The invention provides for using the peroxidase formed by amyloid-β peptide (Aβ) and heme as a measure of the pathology of Alzheimer's Disease. It provides for using this peroxidase in the diagnosis, prevention, and/or treatment of chronic neurodegenerative diseases, especially, but not exclusively, Alzheimer's Disease. This invention can also serve as an assay for the risk of developing such chronic neurodegenerative diseases, especially but not exclusively, Alzheimer's Disease, for determining the progression of said diseases, especially but not exclusively, Alzheimer's Disease, and the effectiveness of other agents in treating or preventing such diseases, especially, but not exclusively, Alzheimer's Disease.

The invention provides methods and compositions for detecting, measuring, modulating and packaging Aβ-heme peroxidase activity. The invention includes ways to measure the peroxidase activity of Aβ-heme, inhibitors of Aβ-heme peroxidase activity, and methods to detect inhibition of Aβ-heme peroxidase activity. Another embodiment is incorporating the method of measuring peroxidase activity of Aβ-heme into screening assays, wherein Aβ-heme peroxidase activity is first used as a reference, a potential inhibiting agent is then contacted with the Aβ-heme, and wherein a reduction of Aβ-heme peroxidase activity indicates that the agent inhibits Aβ-heme peroxidase activity.

In one embodiment, the methods comprise selectively measuring peroxidase activity of Aβ-heme to obtain a measurement of Aβ-heme peroxidase activity, wherein prior to the measuring step, the method may further comprise the step of contacting the Aβ-heme with an inhibitor of Aβ-heme peroxidase activity, and then detecting a resultant inhibition of the Aβ-heme peroxidase activity.

The disclosed methods for measuring peroxidase activity of Aβ-heme may also be incorporated into screening assays, wherein prior to the measuring step the method further comprises the step of contacting the Aβ-heme with a candidate agent under conditions wherein but for the presence of the agent, the Aβ-heme presents a reference Aβ-heme peroxidase activity, and wherein the measuring step detects an agent-biased Aβ-heme peroxidase activity, wherein a reduced agent-biased Aβ-heme peroxidase activity as compared with the reference Aβ-heme peroxidase activity indicates that the agent inhibits Aβ-heme peroxidase activity.

The invention also provides methods of inhibiting Aβ-heme peroxidase activity comprising the step of contacting a mixture comprising Aβ-heme peroxidase with an Aβ-heme peroxidase inhibitor such as hydroxylamine, a diaminophenothiazine, ferulic acid and ferulic acid derivatives, and curcumin, and combinations thereof, and selectively detecting a resultant inhibition in peroxidase activity of the Aβ-heme peroxidase. The contacting step may be effected by coadministering the inhibitor and a cofactor of heme biosynthesis to an individual determined to be in need thereof, particularly wherein the cofactor is iron, copper, zinc or biotin.

The invention also provides related pharmaceutical compositions comprising an inhibitor of Aβ-heme peroxidase activity, and a cofactor of heme biosynthesis, particularly wherein the inhibitor is a hydroxylamine, a diaminophenothiazine or curcumin, and the cofactor is iron, copper, zinc or biotin.

The invention also provides methods of inducing oxidation of a substrate by contacting a substrate determined to be in need of oxidation with Aβ-heme under conditions wherein the Aβ-heme induces oxidation of the substrate, and detecting a resultant oxidation of the substrate, particularly wherein the method further comprises the prior step of determining the substrate is in need of oxidation.

The invention also provides compositions comprising an Aβ-heme complex having predetermined, measured and stabilized peroxidase activity and packaged as an industrial enzyme in a predetermined, measured amount in a sealed and labeled package, particularly solvated in an organic solvent such as ethanol, methanol, and acetone.

DETAILED DESCRIPTION OF THE INVENTION

The inventors have characterized a novel peroxidase formed from Aβ-heme complexes. The invention provides Aβ-heme peroxidase activity as a marker for age-related diseases involving Aβ. The invention provides methods and compositions for detecting, measuring, inhibiting and packaging Aβ-heme peroxidase activity. In one embodiment, the methods comprise selectively measuring peroxidase activity of Aβ-heme to obtain a measurement of Aβ-heme peroxidase activity.

Peroxidase activity of the Aβ-heme complex may be measured or determined using a wide variety of applicable peroxidase assays, including commercially-available assays (e.g. ImmunoPure TMB kit; Pierce Biotechnology, Rockford, Ill.). In one example, the Aβ-heme complex is contacted with an oxidizable substrate under conditions wherein the Aβ-heme catalyzes oxidation of the substrate, and resulting peroxidase activity is measured by detecting oxidation product(s) of the substrate (e.g. see Example 2). In specific embodiments, the substrate is selected from TMB, ABTS, AEC, NC, DAB, Guaiacol, OPD, PPHP, etc.

Selective measurement may be achieved, for example, by using isolated or labeled Aβ-heme peroxidase, an Aβ-heme peroxidase selective substrate, Aβ-heme peroxidase selective reaction conditions such as organic solvents, temperature, pH, ionic strength, cofactors, etc. Selective measurement may also be effected by examining tissue samples that do not present conflicting peroxidase activities, such as blood plasma, cerebral-spinal fluid, etc. A wide variety of noninvasive imaging technologies may be used for selective measurement of Aβ-heme peroxidase, including MRI, ESR, etc. Alternatively tissue samples may be collected, and Aβ-heme peroxidase activity selectively measured therefrom (e.g. using Aβ-heme peroxidase-specific immunoselection or specific ELISA). Increased peroxidase activity relative to normal tissue identifies patient suitability for Aβ-heme peroxidase inhibitor therapy.

In particular embodiments, the methods comprise the step of contacting the Aβ-heme with an inhibitor of Aβ-heme peroxidase activity, and then detecting a resultant inhibition of the Aβ-heme peroxidase activity. Preferred target populations for detecting and/or inhibiting Aβ-heme peroxidase activity are determined to be associated with or at risk for age-related disorders such as Alzheimer's disease and pathologies associated with Down's syndrome. The disclosed methods of selectively measuring peroxidase activity of Aβ-heme can also be used to identify patients with (elevated) Aβ-heme peroxidase activity as suitable for treatment with an Aβ-heme peroxidase inhibitor.

The invention provides methods of inhibiting Aβ-heme peroxidase activity comprising the step of contacting a mixture comprising Aβ-heme peroxidase with an Aβ-heme peroxidase inhibitor such as hydroxylamine (e.g. PCT/US00/29634; PCT/US05/16580), a diaminophenothiazine (e.g. PCT/US06/06320), or ferulic acid, including dimers (e.g. US Pat Pub No. 20040236148), or ferulic acid derivatives, particularly esterified derivatives such gamma-oryzanol and cycloartenyl ferulate, and detecting a resultant inhibition in peroxidase activity of the Aβ-heme peroxidase. The inhibitor can function in different ways, e.g. by directly interfering with peroxidase activity of the active enzyme, or by interfering with active complex formation, such as with metalated porphyrins (e.g. PCT/US06/03315), such as heme with non-iron metals (e.g. Cu, Zn, Sn, etc.).

In particular embodiments, Aβ-heme peroxidase-specific antibodies are used to inhibit activity and/or formation of Aβ-heme peroxidase. The antibodies may be exogenous to the patient, or elicited with Aβ-heme complexes, or Aβ-heme complex-specific immunogens, which are readily produced by screening antibodies elicited by candidate Aβ-heme complex-derived immunogens in animal models against native Aβ-heme.

In some embodiments, particularly wherein the inhibition depletes or depends in part on endogenous heme or heme precursors, the contacting step may be advantageously effected by coadministering the inhibitor and a cofactor of heme biosynthesis to an individual determined to be in need thereof, particularly wherein the cofactor is iron, copper, zinc or biotin.

The invention also provides related pharmaceutical compositions comprising an inhibitor of Aβ-heme peroxidase activity, and a cofactor of heme biosynthesis, particularly wherein the inhibitor is a hydroxylamine, a diaminophenothiazine or curcumin, and the cofactor is iron, copper, zinc or biotin. Dosages are effective yet physiological, typically from 0.1 to 10, or from 0.2 to 5, or from 0.5-1.5, or about 1 times governmental recommended daily allowances (RDA).

The disclosed methods for measuring peroxidase activity of Aβ-heme may also be incorporated into screening assays, wherein prior to the measuring step the method further comprises the step of contacting the Aβ-heme with a candidate agent under conditions wherein but for the presence of the agent, the Aβ-heme presents a reference Aβ-heme peroxidase activity, and wherein the measuring step detects an agent-biased Aβ-heme peroxidase activity, wherein a reduced agent-biased Aβ-heme peroxidase activity as compared with the reference Aβ-heme peroxidase activity indicates that the agent inhibits Aβ-heme peroxidase activity. These screening assays identify agents that modulate (i.e. increase or inhibit) Aβ-heme peroxidase activity, and may be performed as a high-throughput screening assay to identify Aβ-heme peroxidase activity inhibitors in a chemical library.

The invention also provides methods of inducing oxidation of a substrate comprising the step of contacting a substrate determined to be in need of oxidation with Aβ-heme under conditions wherein the Aβ-heme induces oxidation of the substrate, and detecting a resultant oxidation of the substrate. In one embodiment, the method further comprises the prior step of determining that the substrate is in need of oxidation. The oxidation of various substrates by Aβ-heme is described herein (e.g. Example 2).

Aβ-heme peroxidase can be isolated from biological tissues (e.g. using conventional techniques like immunoprecipitation, chromatography, etc.); alternatively, Aβ-heme can be readily prepared using commercially available, synthetic or recombinant Aβ and heme. Solutions of Aβ and heme are prepared and mixed together; the ratio of Aβ to heme is 100:1 to 1:100, preferably 10:1 to 1:10, preferably 2:1, 1:2, or 1:1. The complex self-assembles, and can be visually detected by a change in heme color, e.g. from a greenish-brown to a golden brown color in aqueous solution. The composition can comprise any suitable diluent such as water, a buffer, an organic solvent (e.g. ethanol, methanol, and acetone), etc.

The invention also provides compositions comprising an Aβ-heme complex having predetermined, measured and stabilized peroxidase activity and packaged as an industrial enzyme in a predetermined, measured amount in a sealed and labeled package, particularly solvated in an organic solvent such as ethanol, methanol, and acetone. Packaging of industrial enzymes is pursuant to standards in the art, and involves containing stabilized enzyme in discrete volume, weight or activity unit amounts, in saleable, sealed, labeled packaging. Stabilization can be effected by freeze drying (lyophilization), protein stabilizer reagents, etc. Discrete amounts of the Aβ-heme complex are packaged and labeled with applicable information regarding amount, units of peroxidase activity, etc., and instructions for use (e.g. as an industrial enzyme, in drug screening assays, etc.)

EXAMPLE 1

Preparation of Aβ-Heme Complex

Heme is prepared by dissolving hemin (Frontier Scientific, Logan, Utah) in 0.1 N NaOH to make 5 mM solution. Unless otherwise contraindicated, we use the term "heme" to refer to heme and salts thereof, including hemin, hematine, etc. The heme solution is then diluted in 50 mM Hepes to make 600 µM (pH about 7.4). Amyloid-β (Aβ) peptide (American Peptide, Sunnyvale, Calif.) is dissolved in distilled deionized water to make a 600 µM solution. Aβ is mixed with heme at a 1:1 ratio to make a 300 µM solution of each (this is a 300 μM stock Aβ-heme complex) and incubated for 10-30 minutes in the dark at room temperature to insure complete complexation and removal of possible aggregates. Binding is instantaneous and can be visually detected by the change to hemin's color or by measuring the red shift in the absorbance spectrum of heme. The color changes from a greenish-brown to a golden brown when the heme complexes with Aβ.

EXAMPLE 2

Peroxidase Activity of Aβ-Heme Complex

The peroxidase activity of Aβ-heme was measured by the oxidation of 3,3',5,5'-tetramethylbenzidine (TMB) by $H_2O_2$ by following the increase in absorbance at 652 nm, which allows continuous monitoring of the TMB oxidation product. Alternatively, the reaction was terminated by 4M sulfuric acid, which shifts the absorbance peak of the TMB oxidation product to 450 nm. The peroxidase activity of Aβ-heme was tested in the concentration range of 100-700 nM of the complex for 15-30 min at room temperature.

Several types of organic solvents are known to inactivate enzymes including peroxidases. We tested the effect of ethanol, methanol, and acetone on Aβ-heme peroxidase. Aβ-heme was incubated in the each organic solvent for 10 min. The final percentage of the organic solvent was maintained at 99%. A 50 μl aliquot of Aβ-heme/organic solvent solution was added to 200 μl TMP peroxidase assay kit, and activity of Aβ-heme was monitored by following TMB oxidation at 652 nm. The rate of TMB oxidation was calculated from the first linear 100 seconds of the reaction. The final concentration of Aβ-heme was 0.15 μM. The peroxidase activity of Aβ-heme was not affected by organic solvents, reflecting the stability of the Aβ-heme complex. More than two folds increase in the peroxidase activity of Aβ-heme was seen upon treatment with acetone.

The effect of potential substrates (serotonin and DOPA) on Aβ-heme peroxidase activity was measured by the TMB assay or by HPLC. For the HPLC assay, 100 μM serotonin was incubated with 3 mM $H_2O_2$ and 500 nM Aβ-heme in 50 mM Hepes, pH 7.2. At specific time intervals, the oxidation products of serotonin were analyzed by injecting 23.5 μl from the reaction mixture into RP-HPLC on a 300-×3.9-mm column of Bond-Clone-C18 (Phenomenex) by using as mobile-phase 10% methanol, pH 3. Serotonin or oxidation products were analyzed with a UV-online detector set at 280 nm. The retention time of serotonin was 4.7 minutes. Adding Aβ-heme to serotonin plus $H_2O_2$ decreased the serotonin peak after a 60-min reaction and led to the formation of two oxidation products having retention times of 3.3 and 4.0 min.

EXAMPLE 3

Aβ Induces Heme Synthesis And Iron Uptake

The effect of Aβ on heme synthesis was used to test the biological effect of the Aβ and heme interaction. We expected an increase in heme synthesis due to depletion of regulatory heme if the binding between heme and Aβ occurs in the cell. Aβ at concentrations of 0.1, 1, and 10 μM significantly increased the synthesis of heme in human neuroblastoma (SHSY5Y) cells. A 40% increase in heme synthesis was seen after 2 h incubation with 0.1 μM Aβ. A 4-fold and 13-fold increase in heme synthesis was seen after 1 h of incubation with 1 and 10 μM Aβ, respectively. A 2.5-fold and 18-fold increase in heme synthesis was seen after 2 h of incubation with 1 and 10 μM Aβ, respectively. An increase in the uptake of cofactors of heme biosynthesis is necessary to support heme synthesis. For example, Aβ at concentrations of 0.1, 1, and 10 μM significantly increased the intracellular iron. A 55% increase in iron was seen after 2 h of incubation with 0.1 μM Aβ. A 4-fold and 12.5-fold increase in iron uptake was seen after 1 h of incubation with 1 and 10 μM Aβ, respectively. A 2-fold and 8-fold increase in iron uptake was seen after 2 h of incubation with 1 and 10 μM Aβ, respectively. The exposure of SHSY5Y cells to Aβ was not toxic as measured by trypan blue exclusion tests and compared with controls.

EXAMPLE 4

Inhibition of Peroxidase Activity of Aβ-Heme Complex; Inhibitor Screen

The effect of potential inhibitors of Aβ-heme peroxidase activity was measured by the TMB assay (supra) or by HPLC. The peroxidase activity of Aβ-heme was significantly inhibited by 1 μM curcumin, 100 μM N-benzylhydroxylamine (NBHA), and 10 μM methylene blue. Synthetic N-hydroxylamine and diaminophenothiazine libraries are similarly screened for inhibitors of Aβ-heme peroxidase activity in the same TMB assay, identifying numerous inhibitors including N-hydroxylamines: N-tert-butylhydroxylamine, N-cyclohexylhydroxylamine, N-isopropylhydroxylamine, N-(4-hydroxybutyl)hydroxylamine, N-(2-carboxyethyl)hydroxylamine, N-(benzylcarbonyl)methylhydroxylamine, and N-(acetyl)hydroxylamine, N-(3-nitropropyl)hydroxylamine; diaminophenothiazines: azure A, azure B, azure C, thionine, toluidine blue, methylene blue, new methylene blue, and 1-9-dimethyl methylene blue; and metalated porphyrins: uroporphyrin III, uroporphyrin I, coproporphyrin III, and coproporphyrin I.

EXAMPLES 5-7

Inhibition of Oxidative Damage In Animal Model of Alzheimer's Disease By Administration Aβ-Heme Peroxidase Inhibitors The Tg2576 APPSw transgenic mouse is an animal model for Alzheimer's disease. Methodology for these examples was adapted from a previously reported study that showed reduced oxidative damage in the curcumin-treated Tg2576 APPSw mouse (Lim et al, J. Neurosci (2001) 21:8370-8377). In these examples we compare curcumin-treated mice with mice treated with the Aβ-heme peroxidase inhibitory hydroxylamines and diaminophenothiazines, and metalated porphyrins identified in Example 4 (supra), and combinations of the identified metalated porphyrins and cofactors of heme biosynthesis ((a) iron, (b) biotin, and (c) iron and biotin). The hydroxylamines are administered to achieve 1-2 mg/kg/day dosage; diaminophenothiazines are administered (in drinking water; 100 nM final concentration) to achieve a 1-2 μg/kg/d dosage; and metalated porphyrins are administered to achieve a 25-50 mg/kg/d dosage. Iron and biotin supplementation is provided per kg food at 600 mg/kg and 0.1 mg/kg, respectively. All treatment groups demonstrate reduced oxidative damage, reduced soluble Aβ, and reduced plaque burden compared with control animals.

EXAMPLE 5

Oxidative Damage Is Reduced In Mice Treated With Aβ-Heme Peroxidase Inhibitors Oxidative damage is assessed in Tg– untreated, Tg+ untreated, and Tg+ treated groups using Western blot analysis, in which carbonyl groups on oxidized proteins are derivitized with DNPH and detected using an anti-DNP antibody. Statistical analysis reveals a significant transgene effect in oxidized protein levels. A combined regional analysis of four brain regions reveals that animals treated with our Aβ-heme peroxidase inhibitors have lower levels of oxidized proteins compared with cofactor only, and untreated animals.

EXAMPLE 6

Aβ-Heme Peroxidase Inhibitors Reduce TBS-Soluble Aβ And SDS-Insoluble Aβ (Amyloid)

Previous studies showed that a chronic dose of curcumin significantly reduces insoluble and soluble Aβ in APPSw mice (Lim 2001, supra). To demonstrate this effect in animals treated with our Aβ-heme peroxidase inhibitors, levels of SDS-insoluble Aβ are measured by ELISA in entorhinal cortex, hippocampus, and residual cortex regions. Statistical analysis reveals a significantly enhanced reduction in insoluble Aβ, as compared with control animals.

EXAMPLE 7

Low Doses of Aβ-Heme Peroxidase Inhibitors Reduce Plaque Burden In APPSw Brains To evaluate whether treatment with our Aβ-heme peroxidase inhibitors reduces plaque pathology, cryostat hemibrain sections from Tg+ control and Tg+ treated mice are immunostained with an antibody against Aβ1-13. Statistical analysis reveals a reduction in plaque burden in treated animals.

EXAMPLE 8

Aβ-Heme Peroxidase Inhibitors Reduce Memory Loss And Cognitive Decline

Aβ-heme peroxidase inhibitors reduce memory loss and cognitive decline in 3×Tg-AD mice (Oddo et al., Neuron 39 (2003), 409-421) as determined in established spatial reference and contextual learning paradigms (1).

Aβ-heme peroxidase inhibitors (group I hydroxylamines: N-tert-butylhydroxylamine, N-cyclohexylhydroxylamine, N-isopropylhydroxylamine, N-(4-hydroxybutyl)hydroxylamine, N-(2-carboxyethyl)hydroxylamine, N-(benzylcarbonyl)methylhydroxylamine, and N-(acetyl)hydroxylamine, N-(3-nitropropyl)hydroxylamine; group II diaminophenothiazines: azure A, azure B, azure C, thionine, toluidine blue, methylene blue, new methylene blue, and 1-9-dimethyl methylene blue; and group III metalated porphyrins: uroporphyrin III, uroporphyrin I, coproporphyrin III, and coproporphyrin I were characterized in Example 4 above. Hydroxylamines are provided in food pellets to achieve 1-2 mg/kg/day dosage; diaminophenothiazines are administered (in drinking water; 100 nM final concentration) to achieve a 1-2 μg/kg/day dosage; and metalated porphyrins are provided in food pellets to achieve a 25-50 mg/kg/day dosage.

Morris water maze (MWM). The apparatus used for water maze tasks is a circular aluminum tank (1.5 m diameter) painted white and filled with water maintained at 26° C.-29° C. The maze is located in a room containing several simple visual, extramaze cues. To reduce stress, mice are placed on the platform in both the hidden and cued versions of the task for 10 s prior to the first training trial.

Spatial Reference MWM Training. Mice are trained to swim to a 14 cm diameter circular clear Plexiglas platform submerged 1.5 cm beneath the surface of the water and invisible to the mice while swimming. The platform location is selected randomly for each mouse, but kept constant for each individual mouse throughout training. On each trial, the mouse is placed into the tank at one of four designated start points in a pseudorandom order. Mice are allowed to find and escape onto the submerged platform. If a mouse fails to find the platform within 60 s, it is manually guided to the platform and allowed to remain there for 10 s. After this, each mouse is placed into a holding cage under a warming lamp for 25 s until the start of the next trial. To ensure that memory differences are not due to lack of task learning, mice are given four trials a day for as many days as were required to train the 3×Tg-AD-H and 3×Tg-AD-h mice to criterion (<20 s mean escape latency before the first probe trial was run). To control for overtraining, probe trials are run for each group, both as soon as they reach group criterion and after all groups reach criterion.

Retention of the spatial training is assessed 1.5 hr and again 24 hr after the last training trial. Both probe trials consist of a 60 s free swim in the pool without the platform. Mice are monitored by a camera mounted in the ceiling directly above the pool, and all trials are stored on videotape for subsequent analysis. The parameters measured during the probe trial include (1) initial latency to cross the platform location, (2) number of platform location crosses, and (3) time spent in the quadrant opposite to the one containing the platform during training. For the 6 month training, the target quadrant is changed to avoid savings from previous water maze experience. Target quadrants vary between mice within a group to control for potential differences in the salience of extramaze cues.

Cued MWM Training. The cued task training consists of four consecutive 60 s trials per day (40 s ITI), and begin the first day after the spatial testing ends. Each trial consists of the mouse starting from one of five positions along the side of the water tank. The mouse is given 60 s to find the visible platform (indicated by a striped flag above the water level). If the mouse does not mount the platform within the 60 s, it is manually guided to the platform. A group mean of <20 s escape latency is the required criterion. After mounting the platform, the mouse is immediately removed to a holding cage. The visible platform is moved to different locations between each trial, so that the mouse's starting position and the platform location are unique between trials.

Inhibitory avoidance (IA). For IA, testing begins with a training trial in which a mouse is placed in a lighted chamber; when the mouse crosses over to the dark chamber, it receives a mild (0.25 mA/1 s) footshock. This initial latency to enter the dark (shock) compartment serves as the baseline measure. During the probe trials, 1.5 or 24 hr after training, the mouse is again placed in the light compartment, and the latency to return to the dark compartment (previously associated with shock) measured as an index of passive fear avoidance.

Aβ-heme peroxidase inhibitor treated and untreated 3×Tg-AD mice are evaluated with the foregoing spatial reference and contextual learning paradigms. All treatment groups show reduced impairment during acquisition on the MWM task; improved short- and long-term memory as measured by latencies to cross the platform location, number of platform location crosses, and time spent in the opposite quadrant as compared to untreated mice. Treated mice also demonstrate significant improvements on the visible platform (cued) training in the MWM, and improved retention for contextual fear.

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. As used herein, the singular forms "a," "an," and "the," refer to both the singular as well as plural, unless the context clearly indicates otherwise.

REFERENCES

1. Billings, L. M., et al (2005) Neuron 45, 675-688.
2. Skovronsky, D. M., et al (1998) J. Cell Biol. 141, 1031-1039.
3. Walsh, D. M., et al (2004) Protein Pept. Lett. 11, 213-228.
4. Smith, M. A., et al (2000) Antioxid. Redox. Signal 2, 413-420.
5. Parker, W. D., et al (1994) Neurology 44, 1090-1096.
6. Mutisya, E. M., et al (1994) J. Neurochem. 63, 2179-2184.
7. Connor, J. R., et al (1992) J. Neurosci. Res. 31, 327-335.
8. Gsell, W., et al (2004) Curr. Pharm. Des. 10, 265-293.
9. Atamna, H. & Frey (2004) Proc. Natl. Acad. Sci. USA 101, 11153-11158.
10. Atamna, H., et al (2002) Proc. Natl. Acad. Sci. USA 99, 14807-14812.
11. Atamna, H., Liu, J. & Ames, B. N. (2001) J. Biol. Chem. 276, 48410-48416.
12. Fawcett, J. R., et al (2002) Brain Res. 950, 10-20.
13. Howlett et al, (1997) FEBS Lett. 417, 249-251.

What is claimed is:

1. A method of detecting amyloid-β peptide-heme (Aβ-heme) peroxidase activity, the method comprising measuring peroxidase activity of Aβ-heme.

2. A method of detecting inhibition of Aβ-heme peroxidase activity, the method comprising contacting the Aβ-heme with a compound, wherein a reduction of the Aβ-heme peroxidase activity in the presence of the compound indicates inhibition of the Aβ-heme peroxidase activity.

3. The method of claim 2 further comprising detecting the inhibition of the Aβ-heme peroxidase activity.

4. A method of screening for inhibitors of Aβ-heme peroxidase activity, comprising contacting the Aβ-heme with a candidate agent under conditions wherein but for the presence of the agent, the Aβ-heme presents a reference Aβ-heme peroxidase activity, detecting an agent-biased Aβ-heme peroxidase activity, wherein a reduced agent-biased Aβ-heme peroxidase activity as compared with the reference Aβ-heme peroxidase activity indicates that the agent inhibits Aβ-heme peroxidase activity.

* * * * *

UNITED STATES PATENT AND TRADEMARK OFFICE
CERTIFICATE OF CORRECTION

| | | |
|---|---|---|
| PATENT NO. | : 7,285,396 B1 | Page 1 of 1 |
| APPLICATION NO. | : 11/395925 | |
| DATED | : October 23, 2007 | |
| INVENTOR(S) | : Atamna et al. | |

It is certified that error appears in the above-identified patent and that said Letters Patent is hereby corrected as shown below:

On the Title Page, Item (75)

The last name of the first inventor is spelled: Atamna.

Signed and Sealed this
Tenth Day of May, 2011

David J. Kappos
*Director of the United States Patent and Trademark Office*